United States Patent
Song

(10) Patent No.: US 12,329,970 B2
(45) Date of Patent: Jun. 17, 2025

(54) METHOD AND DEVICE OF DETERMINING OPTIMAL COMPLEX STIMULI FOR TINNITUS TREATMENT

(71) Applicant: NEURIVE Co., Ltd., Gimbae-si (KR)

(72) Inventor: Jae Jun Song, Seoul (KR)

(73) Assignee: NEURIVE Co., Ltd., Gimbae-si (KR)

( * ) Notice: Subject to any disclaimer, the term of this patent is extended or adjusted under 35 U.S.C. 154(b) by 691 days.

(21) Appl. No.: 17/439,001

(22) PCT Filed: Aug. 18, 2020

(86) PCT No.: PCT/KR2020/010948
§ 371 (c)(1),
(2) Date: Sep. 14, 2021

(87) PCT Pub. No.: WO2022/039285
PCT Pub. Date: Feb. 24, 2022

(65) Prior Publication Data
US 2022/0305262 A1    Sep. 29, 2022

(51) Int. Cl.
*A61N 1/36* (2006.01)
*H04R 25/00* (2006.01)

(52) U.S. Cl.
CPC ......... *A61N 1/36036* (2017.08); *H04R 25/75* (2013.01)

(58) Field of Classification Search
None
See application file for complete search history.

(56) References Cited

U.S. PATENT DOCUMENTS

| | | | |
|---|---|---|---|
| 2002/0012438 A1 | 1/2002 | Leysieffer et al. | |
| 2007/0248690 A1 | 10/2007 | Trager | |
| 2011/0295166 A1* | 12/2011 | Dalton | A61B 5/125 601/47 |
| 2017/0353807 A1 | 12/2017 | Lim et al. | |
| 2018/0339148 A1 | 11/2018 | Kong | |

(Continued)

FOREIGN PATENT DOCUMENTS

| CN | 104783808 A | 7/2015 |
|---|---|---|
| CN | 110251825 A | 9/2019 |

(Continued)

OTHER PUBLICATIONS

Russia Office Action of Application No. 2021133967 dated Jun. 14, 2022.

(Continued)

*Primary Examiner* — Ankit D Tejani
(74) *Attorney, Agent, or Firm* — Sughrue Mion, PLLC

(57) ABSTRACT

Proposed are a method and device of determining optimal complex stimuli for tinnitus treatment. The method of determining the optimal complex stimuli for tinnitus treatment includes: identifying one or more sound stimuli selected by a user input from among a plurality of sound stimuli; identifying one or more electrical stimuli selected by the user input from among a plurality of electrical stimuli; determining a first complex stimulus sequence of complex stimuli in which the one or more selected sound stimuli and the one or more selected electrical stimuli are combined; and applying the complex stimuli to a user, wearing a tinnitus treatment device, according to the determined first complex stimulus sequence.

13 Claims, 4 Drawing Sheets

(56) References Cited

U.S. PATENT DOCUMENTS

| | | | |
|---|---|---|---|
| 2019/0224481 A1* | 7/2019 | Wingeier | A61B 5/4836 |
| 2020/0038658 A1* | 2/2020 | Tyler | A61M 21/02 |

FOREIGN PATENT DOCUMENTS

| | | |
|---|---|---|
| EP | 3 170 479 A1 | 5/2017 |
| KR | 10-2002-0058658 A | 7/2002 |
| KR | 10-1468355 B1 | 12/2014 |
| KR | 10-2015-0083663 A | 7/2015 |
| KR | 10-2016-0145911 A | 12/2016 |
| KR | 10-2020-0109707 A | 9/2020 |
| RU | 2 726 923 C2 | 7/2020 |
| WO | 2009/014812 A1 | 1/2009 |
| WO | 2012/168543 A1 | 12/2012 |

OTHER PUBLICATIONS

Russia Patent Grant Decision of Application No. 2021133967 dated Oct. 3, 2022.
Extended European Search Report dated Oct. 24, 2022, issued in European Application No. 20923678.5.
International Search Report dated May 14, 2021, issued in International Application No. PCT/KR2020/010948.

* cited by examiner tinnitus treatment effect score calculation

| order | stimulus method | effect score | effect score recalculation (optional) |
|---|---|---|---|
| #1 | A_A | $S_1=6$ | $T_1 \approx 0.4*S_1+0.3*S_2+0.2*S_3+0.1*S_4$ |
| #2 | A_B | $S_2=9$ | $T_2 \approx 0.0*S_1+0.5*S_2+0.3*S_3+0.2*S_4$ |
| #3 | B_A | $S_3=7$ | $T_3 \approx 0.0*S_1+0.0*S_2+0.6*S_3+0.4*S_4$ |
| #4 | B_B | $S_4=8$ | $T_4 \approx 0.0*S_1+0.0*S_2+0.0*S_3+1.0*S_4$ | weight assignment considering residual suppression effect

|  | $S_1$ | $S_2$ | $S_3$ | $S_4$ |
|---|---|---|---|---|
| #1 | 0.4 | 0.3 | 0.2 | 0.1 |
| #2 | 0.0 | 0.5 | 0.3 | 0.2 |
| #3 | 0.0 | 0.0 | 0.6 | 0.4 |
| #4 | 0.0 | 0.0 | 0.0 | 1.0 |

METHOD AND DEVICE OF DETERMINING OPTIMAL COMPLEX STIMULI FOR TINNITUS TREATMENT

TECHNICAL FIELD

The present invention relates to a method and device of determining optimal complex stimuli for tinnitus treatment.

BACKGROUND ART

In general, tinnitus refers to a state in which a person hears a certain sound stimulus in a situation where there is no external auditory stimulus. There are various causes of tinnitus, but the causes may be a nervous system abnormality, stress or fatigue, noise, otitis externa, etc. As the causes of tinnitus are diverse, the methods for treating tinnitus are also diverse. Currently, 15 or more different treatment methods are used in the Republic of Korea. Examples include drug therapy, tinnitus masking, implantable hearing aid surgery, regular counseling treatment, etc.

However, such methods of tinnitus treatment have limitations in that the methods do not provide a customized treatment method according to patient's tinnitus symptoms. Accordingly, there is a need for a study on a tinnitus treatment method optimized in accordance with the patient's tinnitus symptoms and a treatment effect thereof.

DISCLOSURE

Technical Solution

A method of determining optimal complex stimuli for tinnitus treatment according to an exemplary embodiment includes: identifying one or more sound stimuli selected by a user input from among a plurality of sound stimuli; identifying one or more electrical stimuli selected by the user input from among a plurality of electrical stimuli; determining a first complex stimulus sequence of complex stimuli in which the one or more selected sound stimuli and the one or more selected electrical stimuli are combined; and applying the complex stimuli to a user, wearing a tinnitus treatment device, according to the determined first complex stimulus sequence.

The method of determining the optimal complex stimuli for the tinnitus treatment according to the exemplary embodiment may further include: determining, in a sequence of the complex stimuli, a second complex stimulus sequence in which duration of one or more complex stimuli constituting the sequence is changed; and applying the complex stimuli to the user, wearing the tinnitus treatment device, according to the determined second complex stimulus sequence.

The method may further include: determining, in a sequence of the complex stimuli, a second complex stimulus sequence in which stimulus order of the one or more complex stimuli constituting the sequence is changed; and applying the complex stimuli to the user, wearing the tinnitus treatment device, according to the determined second complex stimulus sequence.

The method of determining the optimal complex stimuli for the tinnitus treatment according to the exemplary embodiment may further include: changing at least one of duration of each of the complex stimuli and stimulus order between the complex stimuli, the complex stimuli being included in the first complex stimulus sequence, so as to determine a second complex stimulus sequence on the basis of each effect diagnosis score for each of the complex stimuli included in the first complex stimulus sequence; and applying the complex stimuli to the user, wearing the tinnitus treatment device, according to the determined second complex stimulus sequence.

The method of determining the optimal complex stimuli for the tinnitus treatment according to the exemplary embodiment may further include: receiving effect diagnosis score information for each complex stimulus sequence through the user input of the user; and determining an optimal complex stimulus sequence from among the plurality of complex stimulus sequences on the basis of the received effect diagnosis score information.

In the method of determining the optimal complex stimuli for the tinnitus treatment according to the exemplary embodiment, the effect diagnosis score information for each complex stimulus sequence may be determined on the basis of each weight for each of the complex stimuli constituting each complex stimulus sequence, and each weight may be determined in consideration of residual suppression effect.

The plurality of sound stimuli may be composed of different sound sources with differences in frequency band and intensity, and the sound sources may include at least one of notch filter music and tinnitus treatment music.

The plurality of electrical stimuli may be composed of different electrical signals with differences in at least one of frequency, intensity, and a waveform.

A device of determining optimal complex stimuli for tinnitus treatment according to the exemplary embodiment includes: a sound stimulus generator configured to generate a sound stimulus; an electrical stimulus generator configured to generate an electrical stimulus; a user input receiver configured to receive a user input; and a controller, wherein the controller may identify one or more sound stimuli selected by the user input received through the user input receiver from among a plurality of sound stimuli, identify one or more electrical stimuli selected by the user input received through the user input receiver from among a plurality of electrical stimuli, determine a first complex stimulus sequence of complex stimuli in which the one or more selected sound stimuli and the one or more selected electrical stimuli are combined, and apply the complex stimuli to the user, wearing a tinnitus treatment device, through the sound stimulus generator and the electrical stimulus generator according to the determined first complex stimulus sequence.

The controller may determine, in a sequence of the complex stimuli, a second complex stimulus sequence in which duration of one or more complex stimuli constituting the sequence is changed, and apply the complex stimuli to the user, wearing the tinnitus treatment device, through the sound stimulus generator and the electrical stimulus generator according to the determined second complex stimulus sequence.

The controller may determine, in a sequence of the complex stimuli, a second complex stimulus sequence in which stimulus order of the one or more complex stimuli constituting the sequence is changed, and apply the complex stimuli to the user, wearing the tinnitus treatment device, through the sound stimulus generator and the electrical stimulus generator according to the determined second complex stimulus sequence.

The controller may change at least one of duration of each of the complex stimuli and stimulus order between the complex stimuli, the complex stimuli being included in the first complex stimulus sequence, so as to determine a second complex stimulus sequence on the basis of each effect diagnosis score for each of the complex stimuli included in the first complex stimulus sequence, and apply the complex stimuli to the user, wearing the tinnitus treatment device, through the sound stimulus generator and the electrical stimulus generator according to the determined second complex stimulus sequence.

The controller may receive effect diagnosis score information for each complex stimulus sequence through the user input of the user, and determine an optimal complex stimulus sequence from among the plurality of complex stimulus sequences on the basis of the received effect diagnosis score information.

In the device of determining the optimal complex stimuli for the tinnitus treatment according to the exemplary embodiment, the effect diagnosis score information for the complex stimulus sequence may be determined on the basis of each weight for each of the complex stimuli constituting the complex stimulus sequence, and each weight may be determined in consideration of residual suppression effect.

Advantageous Effects

According to an exemplary embodiment, more effective treatment of tinnitus may be provided by finding out a combination of personalized sound-electrical complex stimuli optimized for treating tinnitus symptoms of a user, through an optimal complex stimulus determination method for tinnitus treatment.

According to the exemplary embodiment, an optimal tinnitus treatment method may be determined while a tinnitus patient undergoes self-treatment and diagnosis for a long time at home, so that the tinnitus patient who is unable to frequently visit a hospital for the treatment may be treated with the optimal tinnitus treatment.

According to the exemplary embodiment, by providing a complex stimulus sequence composed of various combinations of sound stimuli and electrical stimuli in a process of tinnitus treatment, boredom experienced by the patient may be reduced and adaptation of the human body may be prevented from occurring. In this way, the effectiveness of treatment may be improved.

BEST MODE

Figure 1:
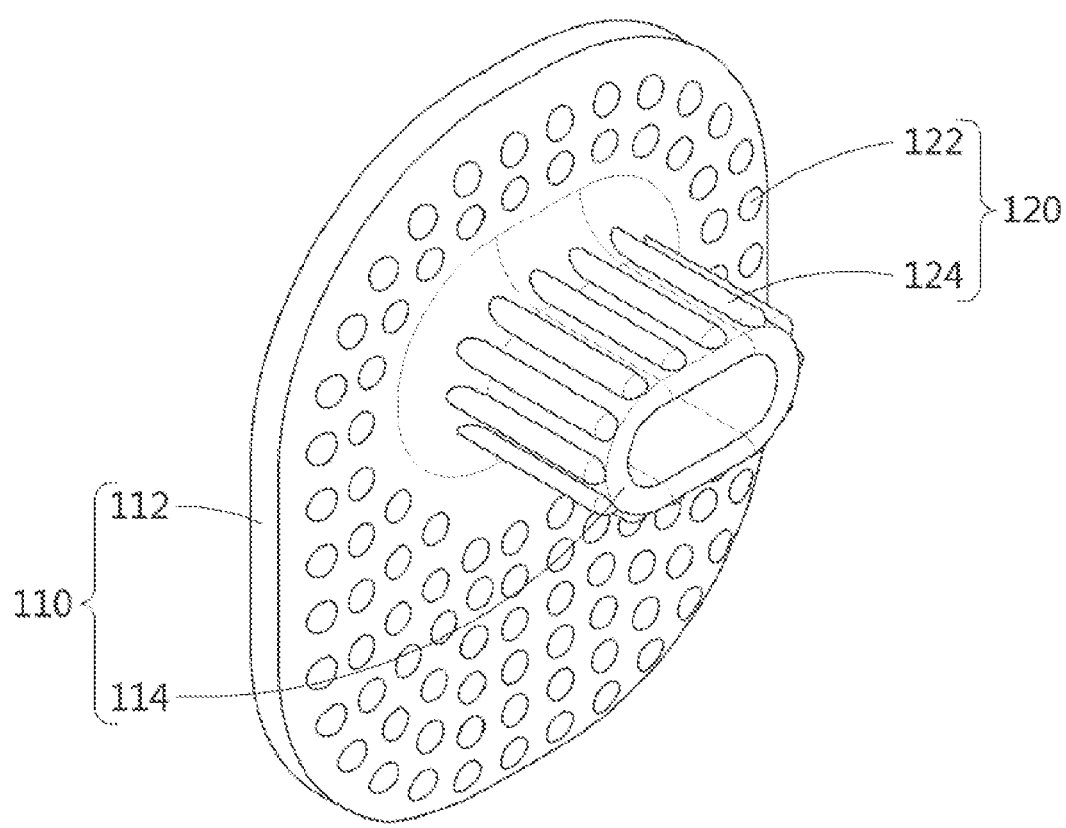
FIG. 1 is a view showing a tinnitus treatment device.

Hereinafter, exemplary embodiments will be described in detail with reference to the accompanying drawings. However, since various changes may be made to the exemplary embodiments, the scope of the patent application is not limited or changed by these exemplary embodiments. It should be understood that all changes, equivalents, or substitutes for the exemplary embodiments are included in the scope of the patent rights.

The terms used in the exemplary embodiments are used for the purpose of description only, and should not be construed as intentional. As used herein, the singular forms are intended to include the plural forms as well, unless the context clearly indicates otherwise. In the present specification, it will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Unless otherwise defined, all terms including technical and scientific terms used herein have the same meaning as commonly understood by one of those skilled in the art to which the present disclosure belongs. It will be further understood that terms as defined in dictionaries commonly used herein should be interpreted as having a meaning that is consistent with their meaning in the context of this specification and the related art and will not be interpreted in an idealized or overly formal sense unless expressly so defined herein.

In the description with reference to the accompanying drawings, regardless of the drawing codes, the same components will be given the same reference numerals and duplicate descriptions of the same components will be omitted. In describing the exemplary embodiment, when it is determined that a detailed description of a known technology related to the present disclosure may unnecessarily obscure the subject matter of the exemplary embodiment, the detailed description thereof will be omitted.

FIG. 1 is a view showing a tinnitus treatment device.

Referring to FIG. 1, the tinnitus treatment device may include a pad 110 and a plurality of stimulus generators 120. The pad 110 may be designed to be mounted inside the ear of a patient receiving tinnitus treatment. In this case, the pad 110 may have a shape of an earphone, but the shape of the pad 110 is not limited thereto, and may have various shapes as long as the pad 110 may be securely mounted inside the ear. Accordingly, a silicone material or an insulating rubber material may be used for the pad 110.

The pad 110 may be divided into a first pad part 112 and a second pad part 114. The first pad part 112 may have a shape capable of contacting the external auditory meatus, and the second pad part 114 may have a shape capable of contacting inside of the ear.

The plurality of stimulus generator 120 may include a sound stimulus generator and an electrical stimulus generator, and the sound stimulus generator and the electrical stimulus generator may be uniformly distributed. The plurality of stimulus generators 120 may generate sound stimuli and electrical stimuli simultaneously or sequentially. In addition, the sound stimulus generator and the electrical stimulus generator constituting the plurality of stimulus generators 120 may be individually controlled. Here, the sound stimulus generator may generate sound stimuli, and the electrical stimulus generator may generate electrical stimuli.

The plurality of stimulus generators 120 may be divided into a first stimulus generator 122 and a second stimulus generator 124. The first stimulus generator 122 is a stimulus generator evenly distributed on the first pad part 112, and may apply sound stimuli and electrical stimuli to a part of the user's external auditory meatus. In addition, the second stimulus generator 124 is a stimulus generator evenly distributed on the second pad part 114, and may apply sound stimuli and electrical stimuli to the inner part of the user's ear.

By wearing the tinnitus treatment device included in the complex stimulus determination device on the ear, a user or a tinnitus patient who desires to receive tinnitus treatment may be provided with the tinnitus treatment according to an optimal complex stimulus sequence determined through the complex stimulus determination device.

Hereinafter, a method of determining complex stimuli will be described in more detail with reference to the drawings.

Figure 2:
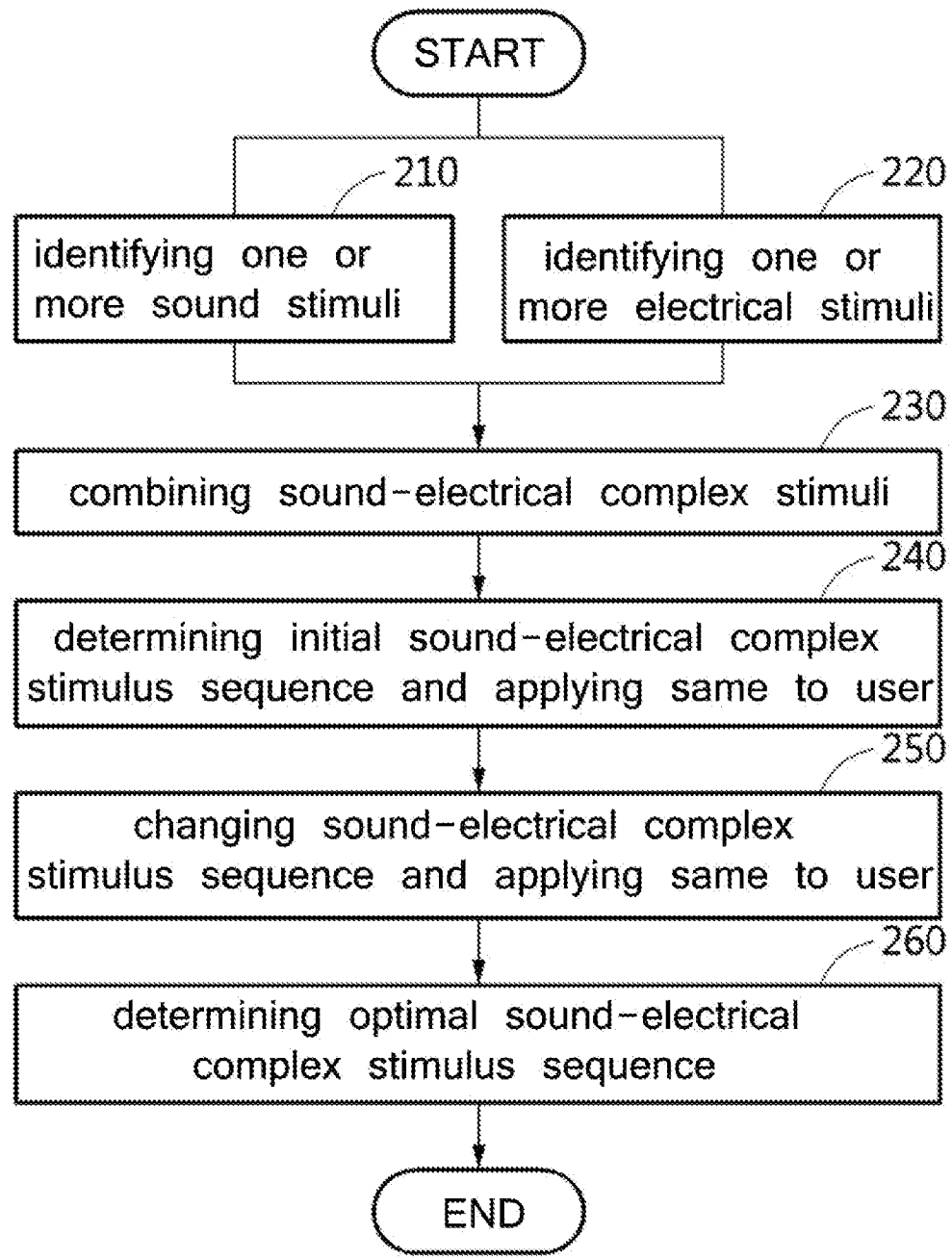
FIG. 2 is a flowchart illustrating operation of a method of determining complex stimuli according to an exemplary embodiment.

FIG. 2 is a flowchart illustrating operation of the method of determining complex stimuli according to the exemplary embodiment.

Referring to FIG. 2, in step 210, from among a plurality of sound stimuli, the complex stimulus determination device may identify one or more sound stimuli selected by a user's input.

In the exemplary embodiment, the complex stimulus determination device may generate each of the plurality of sound stimuli. Here, the plurality of sound stimuli may be composed of different sound sources with differences in frequency band and intensity thereof, and the different sound sources may include notch filter music, tinnitus treatment music, etc.

In the above exemplary embodiment, the user may select one or more sound stimuli from among the plurality of sound stimuli provided from the complex stimulus determination device, or may input each effect diagnosis score for each of the plurality of sound stimuli into the complex stimulus determination device. Here, from among the plurality of sound stimuli provided to the user, the user's selection may include one or more sound stimuli determined to be effective, on the basis of the user's self-diagnosis, in treating tinnitus symptoms experienced by the user. The complex stimulus determination device may identify one or more sound stimuli on the basis of a user input.

In step 220, from among a plurality of electrical stimuli, the complex stimulus determination device may identify one or more electrical stimuli selected by the user's input.

In the exemplary embodiment, the complex stimulus determination device may generate each of the plurality of electrical stimuli. Here, the plurality of electrical stimuli may be composed of different electrical signals having a difference in at least one of a frequency, an intensity, and a waveform.

In the above exemplary embodiment, the complex stimulus determination device may generate each of the plurality of electrical stimuli. The user may select one or more electrical stimuli from among the plurality of electrical stimuli provided from the complex stimulus determination device, or input each effect diagnosis score for each of the plurality of electrical stimuli into the complex stimulus determination device. Here, from among the plurality of electrical stimuli provided by the user, the user's selection may include one or more electrical stimuli determined to be effective, on the basis of the user's self-diagnosis, in treating tinnitus symptoms experienced by the user. The complex stimulus determination device may identify one or more electrical stimuli on the basis of the user input.

In step 230, the complex stimulus determination device may combine, into complex stimuli, the one or more sound stimuli selected by a user and the one or more electrical stimuli selected by the user.

For example, the complex stimulus determination device may apply the plurality of sound stimuli such as sound A, sound B, and sound C to the user, and may apply the plurality of electrical stimuli such as electricity A, electricity B, and electricity C. The user provided with the sound stimuli and electrical stimuli may select sound A, sound C, electricity B, and electricity C among the stimuli. The complex stimulus determination device that received an input of a selection corresponding to the sound A, sound C, electricity B, and electricity C from the user may combine the sound A, sound C, electricity B, and electricity C into complex stimuli. The complex stimuli that may be combined through sound A, sound C, electricity B, and electricity C, which are selected through the user's input, may be a combination of sound A-electricity B, sound A-electricity C, sound C-electricity B, and sound C-electricity C.

In step 240, the complex stimulus determination device may determine an initial complex stimulus sequence composed of the complex stimuli in which the one or more sound stimuli selected from the user and the one or more electrical stimuli selected from the user are combined, and may apply the initial complex stimulus sequence to the user wearing the tinnitus treatment device.

In the exemplary embodiment, by assigning information on the order of applying complex stimuli and duration of one persisting complex stimulus to the complex stimuli combined in step 230, the complex stimulus determination device may determine an initial complex stimulus sequence. In addition, the complex stimuli may be applied to the user, wearing the tinnitus treatment device, according to the determined initial complex stimulus sequence. A user provided with the complex stimuli according to the initial complex stimulus sequence may input, to the complex stimulus determination device, a user input for calculating an effect diagnosis score for the complex stimuli provided according to the initial complex stimulus sequence.

For example, in step 230, it may be assumed that the complex stimuli are combined with sound A-electricity B, sound A-electricity C, sound C-electricity B, and sound C-electricity C. As the initial complex stimulus sequence, complex stimuli of sound A-electricity B (lasting one hour)—sound A-electricity C (lasting one hour)—sound C-electricity B (lasting one hour)—sound C-electricity C (lasting one hour) may be selected. The complex stimulus determination device may provide the complex stimuli composed of sound A-electricity B (lasting one hour)—sound A-electricity C (lasting one hour)—sound C-electricity B (lasting one hour)—sound C-electricity C (lasting one hour) to the user wearing the tinnitus treatment device.

Here, the order in which each complex stimulus constituting the initial complex stimulus sequence is generated and the duration of each complex stimulus may be configured more diversely than those shown in the example.

In step 250, the complex stimulus determination device may change the initial complex stimulus sequence on the basis of each effect diagnosis score for each of the complex stimuli constituting the initial complex stimulus sequence, and provide the changed complex stimulus sequence to the user.

In the above exemplary embodiment, having the initial complex stimulus sequence as the first complex stimulus sequence, the complex stimulus sequence may determine a second complex stimulus sequence in which duration and order corresponding to each of the complex stimuli constituting the first complex stimulus sequence are changed. The second complex stimulus sequence may be determined on the basis of the effect diagnosis score corresponding to each of the complex stimuli constituting the first complex stimulus sequence. In addition, on the basis of the effect diagnosis score corresponding to each of the complex stimuli, the complex stimuli included in the first complex stimulus sequence may be replaced with other complex stimuli.

The complex stimulus determination device may apply the complex stimuli to a user, wearing a tinnitus treatment device, according to the second complex stimulus sequence, and on the basis of a user input capable of determining an effect diagnosis score corresponding to each of the complex stimuli constituting the second complex stimulus sequence, the effect diagnosis score for the second complex stimulus sequence may be calculated. The complex stimulus determination device may repeat both a process of changing duration in which each of the complex stimuli constituting the second complex stimulus sequence persists and occurrence order thereof and a process of calculating the effect diagnosis score for the changed complex stimulus sequence.

In step 260, the complex stimulus determination device may determine an optimal complex stimulus sequence.

An effect diagnosis score for the complex stimulus sequence may be calculated on the basis of an input related to preference for each of the complex stimuli and input by a user provided with the complex stimuli according to the complex stimulus sequence. Here, effect diagnosis score information for the complex stimulus sequence may be determined on the basis of each weight for each of the complex stimuli constituting the complex stimulus sequence. Each weight for each of the complex stimuli may be determined in consideration of residual suppression effect. Here, the residual suppression effect means that a shielding effect to reduce tinnitus persists for a predetermined period of time even after shielding sound is stopped.

The complex stimulus sequence determined to have the highest effect diagnosis score may be determined as the optimal complex stimulus sequence. That is, a sequence composed of the complex stimuli determined to be most effective in alleviating a user's tinnitus symptom may be the optimal complex stimulus sequence.

Figure 3:
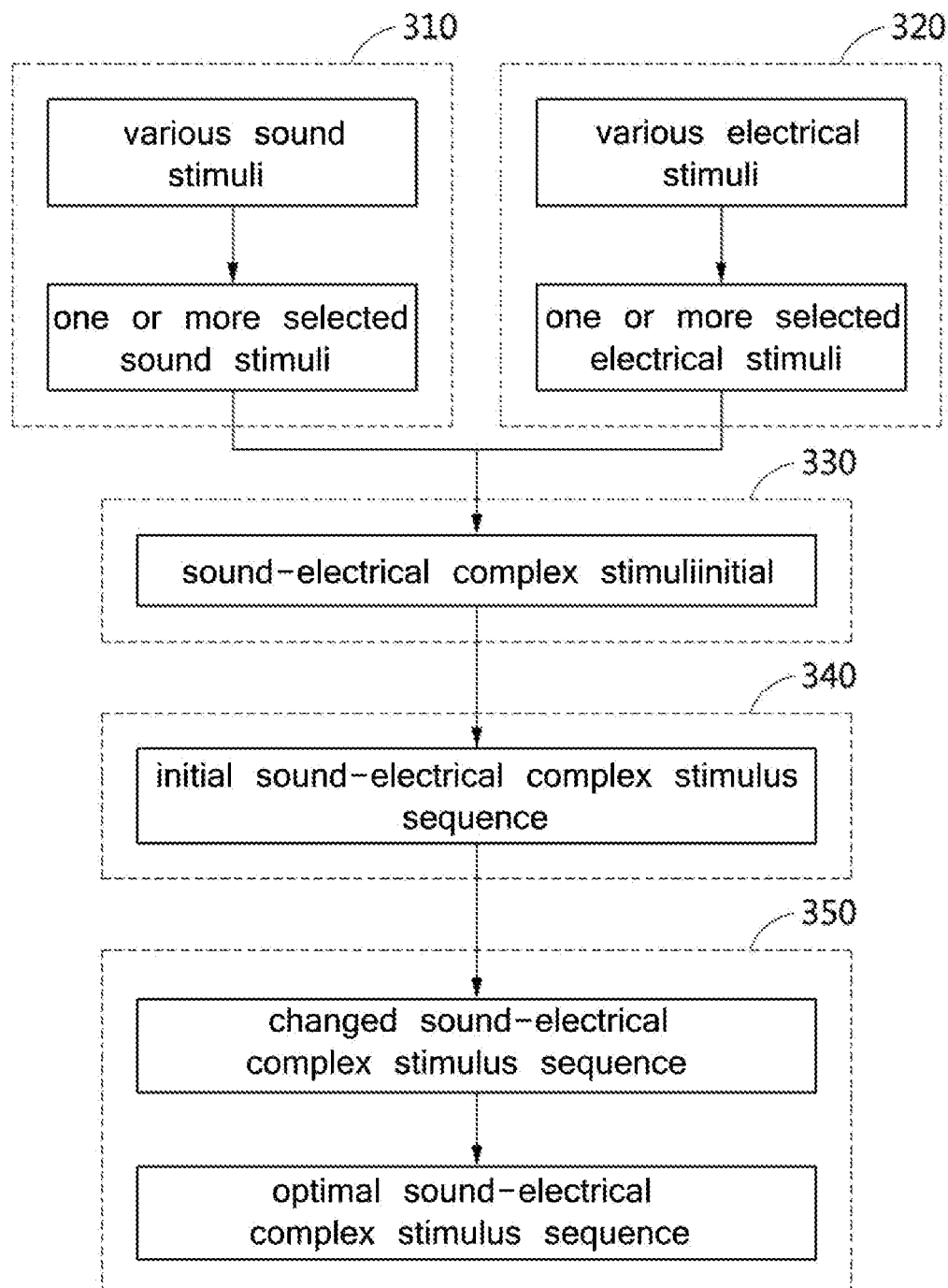
FIG. 3 is a view illustrating a process of determining complex stimuli according to the exemplary embodiment.

FIG. 3 is a view illustrating a process of determining complex stimuli according to the exemplary embodiment.

Referring to FIG. 3, in step 310, the complex stimulus determination device may apply each of the sound stimuli included in the plurality of sound stimuli to the ear canal of a user wearing a tinnitus treatment device. In addition, the complex stimulus determination device may identify one or more sound stimuli on the basis of a user input related to the effect of each of the sound stimuli.

The plurality of sound stimuli may be selected on the basis of user information from among the sound stimuli that the complex stimulus determination device may generate. The user information may include: age, gender, and disease of a user, user's tinnitus status (e.g., both frequency and magnitude of tinnitus) measured through a tinnitus measuring device, and user's hearing loss status measured by an audiometric meter. The complex stimulus determination device may receive the user information through a user input receiver, and may select the plurality of sound stimuli for alleviating tinnitus symptoms of a user on the basis of the received user information. The complex stimulus determination device may provide list information on the plurality of sound stimuli to the user through a display window of the complex stimulus determination device. In addition, the plurality of sound stimuli may be the different sound sources with differences in frequency band and intensity thereof. The sound sources different from each other may include notch filter music and tinnitus therapy music.

One or more sound stimuli may be selected from among the plurality of sound stimuli on the basis of an input of a user provided with the plurality of sound stimuli. Here, the one or more sound stimuli may be determined on the basis of each effect diagnosis score according to the user input, or may be determined by user's selection as well. The effect diagnosis score according to the user input may be calculated on the basis of a user's response to a questionnaire corresponding to each of the sound stimuli, or on the basis of a direct score input. In addition, the effect diagnosis score calculated according to the user input may refer to as a user's preference score for each individual sound stimulus.

In step 320, the complex stimulus determination device may apply each of the electrical stimuli included in the plurality of electrical stimuli to the user wearing the tinnitus treatment device. In addition, the complex stimulus determination device may identify one or more electrical stimuli on the basis of a user input related to the effect of each of the electrical stimuli.

The plurality of electrical stimuli may be selected on the basis of user information and electrical resistance characteristics of the skin inside the user's ear. The user information may include the user's age, gender, and disease. Through a user input receiver, the complex stimulus determination device may take an input of user information or receive the user information, and may select the plurality of electrical stimuli for alleviating the tinnitus symptoms of the user on the basis of the received user information. The complex stimulus determination device may provide the list information on the plurality of electrical stimuli to the user through the display window of the complex stimulus determination device. In addition, the plurality of electrical stimuli may be composed of different electrical signals with differences in frequency, intensity, and waveform thereof.

One or more electrical stimuli may be selected from among the plurality of electrical stimuli on the basis of an input of a user provided with the plurality of electrical stimuli. Here, the one or more electrical stimuli may be selected on the basis of each effect diagnosis score according to the user input, or may be selected by a user's selection. The effect diagnosis score according to the user input may be calculated on the basis of a user's response to a questionnaire corresponding to each of the electrical stimuli, and on the basis of a direct score input. The effect diagnosis score calculated according to the user input may mean the user's preference score for each individual electrical stimulus.

In step 330, the complex stimulus determination device may combine the one or more selected sound stimuli and the one or more electrical stimuli into complex stimuli.

In step 340, the complex stimulus determination device may determine an initial complex stimulus sequence. In the exemplary embodiment, the initial complex stimulus sequence may be the same as the first complex stimulus sequence. The complex stimulus determination device may apply the complex stimuli constituting the first complex stimulus sequence to the user according to the first complex stimulus sequence.

In step 350, the complex stimulus determination device may convert the first complex stimulus sequence into a second complex stimulus sequence on the basis of each effect diagnosis score for each of the complex stimuli constituting the first complex stimulus sequence of the user. The optimal complex stimulus sequence may be determined through a repetitive process in which an effect diagnostic score is calculated on the basis of the second complex stimulus sequence, and duration and the occurrence order of the complex stimuli constituting the second complex stimulus sequence are changed on the basis of the calculated effect diagnosis score.

In the exemplary embodiment, the user may input a user input for the first complex stimulus sequence provided in step 340 to the complex stimulus determination device, and an effect diagnosis score may be calculated on the basis of the user input. The effect diagnosis score for the first complex stimulus sequence may be calculated on the basis of a user's response to a questionnaire corresponding to the first complex stimulus sequence. The effect diagnosis score may be provided with: each effect diagnosis score for each complex stimulus constituting the first complex stimulus sequence; and an effect diagnosis score for the first complex stimulus sequence calculated on the basis of each effect diagnosis score for each complex stimulus.

The occurrence order and duration of each of the complex stimuli constituting the first complex stimulus sequence may be changed on the basis of the effect diagnosis score for the first complex stimulus sequence. In addition, a configuration of the first complex stimulus sequence may be changed. The changed first complex stimulus sequence may be a second complex stimulus sequence. The complex stimulus determination device may calculate an effect diagnosis score for the second complex stimulus sequence on the basis of each effect diagnosis score of each complex stimulus constituting the second complex stimulus sequence.

The optimal complex stimulus sequence may be determined through a repetitive process in which an effect diagnostic score for the complex stimulus sequence is calculated on the basis of each effect diagnosis score of each complex stimulus constituting the complex stimulus sequence, and the complex stimulus sequence is changed on the basis of the calculated effect diagnosis score. Among the complex stimuli constituting the complex stimulus sequence, a complex stimulus having a relatively low effect diagnosis score of tinnitus treatment may be replaced with a complex stimulus having a relatively high effect of tinnitus treatment. In addition, in a complex stimulus having the relatively low effect diagnosis score of tinnitus treatment, duration of the complex stimulus may be decreased, and in a complex stimulus having the relatively high effect of tinnitus treatment, duration of the complex stimulus may be increased. For example, the complex stimulus determination device may replace some of a plurality of sound-electrical complex stimuli constituting the individual sound-electrical complex stimulus sequence with another individual sound-electrical complex stimulus, or change (e.g., increase or decrees) stimulus duration of some of the sound-electrical complex stimuli from among the plurality of sound-electrical complex stimuli constituting an individual sound-electrical complex stimulus sequence. In this way, the complex stimulus determination device may determine the optimal complex stimulus sequence.

Each effect diagnosis score of tinnitus treatment for each complex stimulus constituting the complex stimulus sequence may be calculated through a user input, and may be recalculated by giving different weights to each effect diagnosis score of tinnitus treatment for each complex stimulus, in consideration of the residual suppression effect of nerve stimulation.

Figures 4, 5:
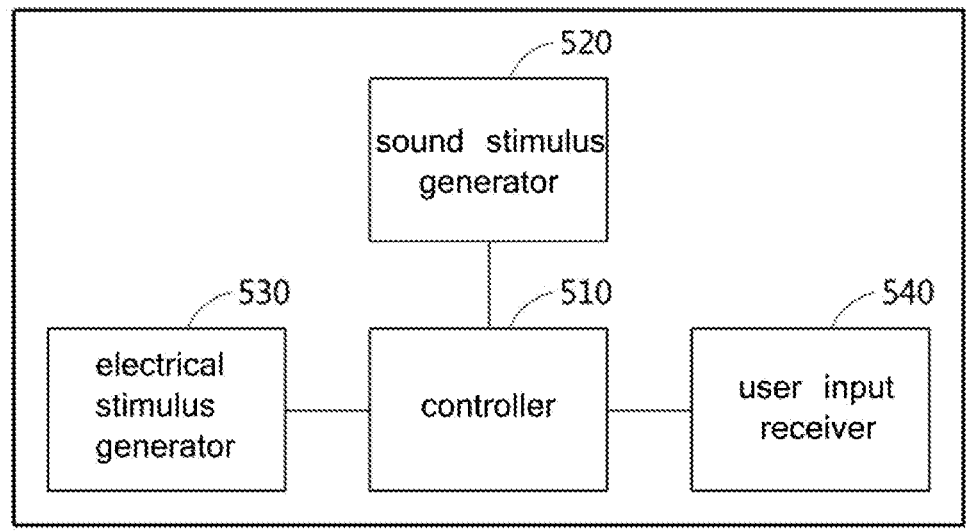
FIG. 4 is a calculation table of effect diagnosis scores for tinnitus treatment effects according to the exemplary embodiment.
FIG. 5 is a view showing a configuration of a complex stimulus determination device according to the exemplary embodiment.

FIG. 4 is a calculation table of effect diagnosis scores for a tinnitus treatment effect according to the exemplary embodiment. Referring to FIG. 4, it may be seen that there is a difference between effect diagnosis scores of complex stimuli input from a user and effect diagnosis scores of the complex stimuli given weights in consideration of the residual suppression effect. The complex stimulus determination device may apply each of the complex stimuli constituting the complex stimulus sequence to the user wearing the tinnitus treatment device, and may receive an evaluation of each of the complex stimuli from the user after a predetermined period of time. When each complex stimulus is applied and some of time intervals are given, the effect diagnosis scores input by the user may vary depending on the order in which the complex stimuli are applied and the time intervals. To compensate for such variation, different weights may be assigned to the effect diagnosis scores in consideration of the residual suppression effect of the nerve stimulation.

FIG. 5 is a view showing the configuration of the complex stimulus determination device according to the exemplary embodiment.

Referring to FIG. 5, the complex stimulus determination device may include: a controller 510, a sound stimulus generator 520, an electrical stimulus generator 530, and a user input receiver 540. In addition, according to the exemplary embodiment, the complex stimulus determination device may further include: a database (not shown) capable of storing various sound stimuli and electrical stimuli; and a display (not shown) capable of displaying information on the sound stimuli, the electrical stimuli, etc.

In the exemplary embodiment, the controller 510 may control the overall operation of the complex stimulus determination device. The controller 510 may perform one or more operations related to the operations of the complex stimulus determination device described with reference to FIGS. 1 to 4.

For example, the controller 510 may identify one or more sound stimuli selected by the user input from among the plurality of sound stimuli, identify one or more electrical stimuli selected by the user input from among the plurality of electrical stimuli, determine a sequence of complex stimuli in which the one or more selected sound stimuli and the one or more selected electrical stimuli are combined, and control the sound stimulus generator 520 and the electrical stimulus generator 530 so that the complex stimuli may be applied to the user, wearing the tinnitus treatment device, according to the first complex stimulus sequence.

The sound stimulus generator 520 and the electrical stimulus generator 530 may respectively generate sound stimuli and electrical stimuli so that the user wearing the tinnitus treatment device may receive the sound stimuli and electrical stimuli. The sound stimulus generator 520 and the electrical stimulus generator 530 may be operated individually or may be operated simultaneously.

The user input receiver 540 may receive a user input. In order to select the plurality of sound stimuli and the plurality of electrical stimuli, which are to be provided to the user wearing the tinnitus treatment device, the user input receiver 540 may receive the user input for the questionnaire from the user. Here, the questionnaire may be displayed through the display. In addition, after the plurality of sound stimuli and the plurality of electrical stimuli are applied to the user, the user input receiver 540 may receive the user input related to selection of the plurality of sound stimuli and the plurality of electrical stimuli, and receive, from the user, the user input related to the user's effect diagnosis score on the complex stimulus sequence.

The device described above may be implemented as a hardware component, a software component, and/or a combination of the hardware component and the software component. For example, devices and components described in the exemplary embodiments may be implemented by using one or more general purpose computers or special purpose computers, including, for example, a processor, a controller, an arithmetic logic unit (ALU), a digital signal processor, a microcomputer, a field programmable gate array (FPGA), programmable logic unit (PLU), microprocessor, or any other device capable of executing and responding to instructions. The processing device may execute an operating system (OS) and one or more software applications running on the operating system. The processing device may also access, store, manipulate, process, and generate data in response to the execution of the software. Sometimes it is described such that one processing device is used for convenience of understanding, but those skilled in the art will recognize that the processing device may include a plurality of processing elements and/or a plurality of types of processing elements. For example, the processing device may include a plurality of processors, or include one processor and one controller. In addition, other processing configurations with such as parallel processors are also possible.

The software may include a computer program, a code, an instruction, or a combination of one or more thereof, and may be configured to enable the processing device to operate as desired or command the processing device independently or collectively. In order to be interpreted by or to provide the instructions or data to the processing device, software and/or data may be embodied permanently or temporarily in any type of machine, component, physical device, virtual equipment, computer storage medium or device, or transmitted signal wave. Software may be distributed over networked computer systems, and stored or executed in a distributed manner. Software and data may be stored in one or more computer-readable recording media.

The method according to the exemplary embodiment may be implemented in the form of program instructions that may be executed through various computer means, and may be recorded in computer-readable media. The computer-readable media may include: program instructions, data files, data structures, and the like individually or in combination. The program instructions recorded on the media may be specially designed and configured for the exemplary embodiment, or may be known and available to those skilled in the art of computer software. Examples of the computer-readable recording media include: magnetic media such as hard disks, floppy disks, and magnetic tapes; optical media such as CD-ROMs and DVDs; magneto-optical media such as floptical disks; and a hardware device specially configured to store and execute program instructions, the hardware device including such as ROM, RAM, flash memory, etc. Examples of program instructions include not only machine language codes such as those generated by a compiler, but also high-level language codes that may be executed by a computer using an interpreter or the like. The hardware device described above may be configured to operate as one or more software modules to perform the operation of the exemplary embodiment, and vice versa.

As described above, although the exemplary embodiments have been described with reference to the limited exemplary embodiments and drawings, various modifications and variations are possible from the above description by those skilled in the art. For example, appropriate results may be achieved even when the described techniques are performed in a different order than that of the described method, and/or the described components of the system, structure, device, circuit, and the like are coupled to each other or combined in a different form than the described method, or replaced or substituted by other elements or equivalents.

Therefore, other implementation, other exemplary embodiments, and equivalents to the claims also fall within the scope of the following claims.

The invention claimed is:

1. A method of determining optimal complex stimuli for tinnitus treatment, the method comprising:
   identifying two or more sound stimuli selected by a user input from among a plurality of sound stimuli;
   identifying two or more electrical stimuli selected by the user input from among a plurality of electrical stimuli;
   determining a first complex stimulus sequence of a plurality of complex stimuli in which the two or more selected sound stimuli and the two or more selected electrical stimuli are combined, wherein each of the plurality of complex stimuli consists of a sound stimulus selected from among the two or more sound stimuli and an electrical stimulus selected from among the two or more electrical stimuli;
   applying the plurality of complex stimuli in the first complex stimulus sequence to a user, wearing a tinnitus treatment device, according to the determined first complex stimulus sequence;
   changing at least one of a duration of each of one or more complex stimuli among the plurality of complex stimuli in the first complex stimulus sequence and a stimulus order between two or more complex stimuli among the plurality of complex stimuli in the first complex stimulus sequence on the basis of an effect diagnosis score for each of the plurality of complex stimuli in the first complex stimulus sequence;
   determining a second complex stimulus sequence of the plurality of complex stimuli based on the changed at least one of the duration and the stimulus order; and
   applying the plurality of complex stimuli in the second complex stimulus sequence to the user, wearing the tinnitus treatment device, according to the determined second complex stimulus sequence.

2. The method of claim 1, wherein the determining of the second complex stimulus sequence comprises:
   determining the second complex stimulus sequence based on change in the duration of each of the one or more complex stimuli among the plurality of complex stimuli in the first complex stimulus sequence.

3. The method of claim 1, wherein the determining of the second complex stimulus sequence comprises:
   determining the second complex stimulus sequence based on change in the stimulus order of the two or more complex stimuli among the plurality of complex stimuli in the first complex stimulus sequence.

4. The method of claim 1, further comprising:
   receiving effect diagnosis score information for each complex stimulus sequence through the user input of the user; and
   determining an optimal complex stimulus sequence from among the plurality of complex stimulus sequences on the basis of the received effect diagnosis score information.

5. The method of claim 4, wherein the effect diagnosis score information for each complex stimulus sequence is determined on the basis of a weight for each of the complex stimuli constituting each complex stimulus sequence, and each weight is determined in consideration of residual suppression effect.

6. The method of claim 1, wherein the plurality of sound stimuli is composed of different sound sources with differences in frequency band and intensity, and the sound sources include at least one of notch filter music and tinnitus treatment music.

7. The method of claim 1, wherein the plurality of electrical stimuli is composed of different electrical signals with differences in at least one of frequency, intensity, and a waveform.

8. A computer-readable recording media configured to record a program for performing the method of claim 1.

9. A device of determining optimal complex stimuli for tinnitus treatment, the device comprising:
- a sound stimulus generator configured to generate a sound stimulus;
- an electrical stimulus generator configured to generate an electrical stimulus;
- a user input receiver configured to receive a user input; and
- a controller, wherein the controller:
- identifies two or more sound stimuli selected by the user input received through the user input receiver from among a plurality of sound stimuli,
- identifies two or more electrical stimuli selected by the user input received through the user input receiver from among a plurality of electrical stimuli,
- determines a first complex stimulus sequence of a plurality of complex stimuli in which the two or more selected sound stimuli and the two or more selected electrical stimuli are combined, wherein each of the plurality of complex stimuli consists of a sound stimulus selected from among the two or more sound stimuli and an electrical stimulus selected from among the two or more electrical stimuli,
- applies the plurality of complex stimuli in the first complex stimulus sequence to the user, wearing a tinnitus treatment device, through the sound stimulus generator and the electrical stimulus generator according to the determined first complex stimulus sequence,
- changes at least one of a duration of each of one or more complex stimuli among the plurality of complex stimuli in the first complex stimulus sequence and a stimulus order between two or more complex stimuli among the plurality of complex stimuli in the first complex stimulus sequence on the basis of an effect diagnosis score for each of the plurality of complex stimuli in the first complex stimulus sequence,
- determines a second complex stimulus sequence of the plurality of complex stimuli based on the changed at least one of the duration and the stimulus order, and
- applies the plurality of complex stimuli in the second complex stimulus sequence to the user; wearing the tinnitus treatment device, through the sound stimulus generator and the electrical stimulus generator according to the determined second complex stimulus sequence.

10. The device of claim 9, wherein the controller determines the second complex stimulus sequence based on change in the duration of each of the one or more complex stimuli among the plurality of complex stimuli in the first complex stimulus sequence.

11. The device of claim 9, wherein the controller determines the second complex stimulus sequence based on change in the stimulus order of the two or more complex stimuli among the plurality of complex stimuli in the first complex stimulus sequence.

12. The device of claim 9, wherein the controller receives effect diagnosis score information for each complex stimulus sequence through the user input of the user, and
- determines an optimal complex stimulus sequence from among the plurality of complex stimulus sequences on the basis of the received effect diagnosis score information.

13. The device of claim 12, wherein the effect diagnosis score information for the complex stimulus sequence is determined on the basis of a weight for each of the complex stimuli constituting the complex stimulus sequence, and
- each weight is determined in consideration of residual suppression effect.

* * * * *